United States Patent [19] [11] E Patent Number: Re. 32,271
Husain et al. [45] Reissued Date of Patent: Oct. 28, 1986

[54] ISOLATION OF PLASMINOGEN ACTIVATORS USEFUL AS THERAPEUTIC AND DIAGNOSTIC AGENTS

[76] Inventors: Syed S. Husain, 139 Upland Ave., Newton, Mass. 02161; Boguslaw Lipinski, 97 Beaumont Ave., Newtonville, Mass. 02160; Victor Gurewich, 11 Reservoir St., Cambridge, Mass. 02161

[21] Appl. No.: 727,807

[22] Filed: Apr. 26, 1985

Related U.S. Patent Documents

Reissue of:
[64] Patent No.: 4,381,346
Issued: Apr. 26, 1983
Appl. No.: 182,976
Filed: Sep. 2, 1980

U.S. Applications:
[63] Continuation-in-part of Ser. No. 93,246, Nov. 13, 1979, abandoned.

[51] Int. Cl.[4] ..... C12N 9/72; C12N 9/48
[52] U.S. Cl. ..... 435/215; 435/212; 424/2; 425/1.1
[58] Field of Search ..... 435/215, 212, 216, 217

[56] References Cited

U.S. PATENT DOCUMENTS

| | | | |
|---|---|---|---|
| 2,961,382 | 11/1960 | Singher et al. | 195/68 |
| 2,983,647 | 5/1961 | Kjeldgaard et al. | 167/73 |
| 2,989,440 | 6/1961 | Singher et al. | 195/66 |
| 3,042,667 | 7/1962 | Flodin et al. | 260/209 |
| 3,140,984 | 7/1964 | Tosoni et al. | 195/66 |
| 3,226,304 | 12/1965 | Siiteri et al. | 435/216 |
| 3,234,106 | 2/1966 | Hink, Jr. et al. | 435/217 |
| 3,256,158 | 6/1966 | White | 195/66 |
| 3,723,251 | 3/1973 | Ogawa et al. | 195/66 B |
| 3,755,083 | 8/1973 | Novak | 195/66 B |
| 3,812,245 | 5/1974 | Dugan | 424/1 |
| 3,933,996 | 1/1976 | Charlton et al. | 424/1 |
| 3,939,258 | 2/1976 | Niemann | 424/1 |
| 3,957,582 | 5/1976 | Streid et al. | 195/66 B |
| 4,025,390 | 5/1977 | Urakawa et al. | 195/66 B |
| 4,036,945 | 7/1977 | Haber | 424/1 |
| 4,094,965 | 6/1978 | Layne et al. | 424/1.5 |
| 4,160,697 | 7/1979 | Chibata et al. | 435/194 |
| 4,165,258 | 8/1975 | Pye et al. | 435/212 |
| 4,258,030 | 3/1981 | Sasaki et al. | 435/215 |
| 4,286,063 | 8/1981 | Suyama | 435/215 |

FOREIGN PATENT DOCUMENTS 1068817 5/1967 United Kingdom .

OTHER PUBLICATIONS

Chemical Abstracts, vol. 89, No. 7, Aug. 14, 1978, Abstract No. 57189K, pp. 91-102.
Chemical Abstracts, vol. 77 No. 17, Oct. 23, 1972, Abstract No. 112034K, p. 250.
Chemical Abstracts, vol. 93, No. 23, Dec. 8, 1980, Abstract No. 216875g, p. 185.
Acta Chemica Scandica, vol. 12, No. 9, 1958, pp. 1825-1829.
Bernik, Maria B. and E. P. Oller, "Increased Plasminogen Activator (Urokinase) in Tissue Culture after Fibrin Deposition," *The Journal of Clinical Invest.* vol. 52 (Apr. 1973) pp. 823-834.
Bernik, Maria B., W. F. White, E. D. Olber, and H. C. Kwaan, "Immunologic Identify of Plasminogen Activator in Human Urine, Heart, Blood Vessels and Tissue Culture," *J. Lab. Clin. Med.*, vol. 84, No. 4 (10/74) pp. 546-558.
Nolan, C., L. S. Hall, G. H. Barlow, and I. I. E. Tribby, "Plasminogen Activator from Human Embryonic Kidney Cell Cultures," *Biochimica et Biophysica Acta*, vol. 496, No. 2 (Feb. 28, 1977) pp. 384-400.
Barlow, G. H., A. Reuter and I. Tribby, "Biosynthesis of Plasminogen Activator by Tissue Culture Technique," *Vascular Surgery*, pp. 406-411.
Bernik, M. B., et al., "Production of Two Immunologically Distinct Plasminogen Activators by Human Tissue in Culture," *Thrombosis and Haemostasis*, VIIth International Congress on Thrombosis and Haemostasis, 7/16/79, Abstract 0989, p. 414.
A. J. Johnson, et al. "Urinary Urokinase-Two Molecules or One", pp. 59-67 in book entitled *Thrombosis and Urokinase*, edited by R. Poletti and S. Sherry, Academic Press 1977.
Lesuk et al., *Throm. Diathes*, Haemorrh., vol. 18, p. 293 (1967).
Gunzler, Wolfgang, et al., "The Primary Structure of High Molecular Mass Urokinase from Human Urine", *Hoppe-Seyler's Z. Physiol. Chem*, pp. 1155-1165, Oct. 1982, A chain, p. 1158.

(List continued on next page.)

*Primary Examiner*—Lionel M. Shapiro

[57] ABSTRACT

The existence of high fibrin-affinity urokinase is discovered by an isolation procedure using fibrin precipitated on an adsorptive-solid matrix. By the method described, the high affinity form of plasminogen activator can be isolated directly from urine or from kidney tissue culture medium. The method is economical and provides a relatively high yield of the activator. The high affinity that this plasminogen activator has for fibrin is a property that makes it an improved thrombolytic agent and when radiolabelled provides a new diagnostic agent for the specific detection of fibrin thrombi through nuclear scanning. The newly-isolated plasminogen activator has the following characteristics: a molecular weight of about 56,000 Daltons, a specific activity of about 40,000-50,000 CTA units/mg, the appearance of a single chain structure and a high affinity for fibrin.

11 Claims, No Drawings

OTHER PUBLICATIONS

Verde, P. et al., "Identification and Primary Sequence of an Unspliced Human Urokinase Poly (A)+RNA", Proc. Natl. Acad. Sci. USA, vol. 81, 1984, pp. 4727–4731.

Steffens, Gerd J., et al. "The Complete Amino Acid Sequence of Low Molecular Mass Urokinase from Human Urine", *Hoppe-Seyler's Z. Physiol. Chem.*, pp. 1043–1058, Sep. 1982, B chain, p. 1050.

White, W. F. et al., "The Isolation and Characterization of Plasminogen Activators (Urokinase) from Human Urine," *Biochemistry*, vol. 5, No. 7 (Jul., 1966) pp. 2160–2169.

Barlow, G. H., et al., "Characterization of the Plasminogen Activator Isolated from Human Embryo Kidney Cells: Comparison with Urokinase," *Thrombosis Research*, vol. 1 (Jun. 1972) pp. 201–208.

Bernik, Maria B., et al. "Inhibitors of Fibrinolysis in Human Tissues in Culture," *American Journal of Physiology*, vol. 227, No. 3 (Sep. 1971) pp. 916–921.

Pye et al., "Purification of Urokinase by Affinity Chromatography" pp. 43–58 of book entitled *Thrombosis and Urokinase*, edited by R. Paoletti and S. Sherry, Academic Press 1977.

Bernik, Maria, et al., "Plasminogen Activator and Proactivator (Urokinase Precursor) in Lung Cultures," *JAMWA*, vol. 31, No. 12 (Dec. 1976) pp. 465–472.

ISOLATION OF PLASMINOGEN ACTIVATORS USEFUL AS THERAPEUTIC AND DIAGNOSTIC AGENTS

Matter enclosed in heavy brackets [ ] appears in the original patent but forms no part of this reissue specification; matter printed in italics indicates the additions made by reissue.

This application is a continuation-in-part of Ser. No. 93,246, filed Nov. 13, 1979, now abandoned.

BACKGROUND OF THE INVENTION

This invention relates to the preparation of plasminogen activators useful as therapeutic and diagnostic agents.

It has been recognized that plasminogen activators are useful in the treatment of blood clots. By introduction of such an activator to a human blood stream in sufficient quantities and duration, a blood clot that has occurred can be dissolved.

The procedures used in the past for isolating plasminogen activators have been characterized by their complexity and costliness. In the case, for instance, of urokinase, the plasminogen activator found in urine, the yield of the known commercial process is so low that a great quantity of urine must be collected and processed in order to treat a single patient. Isolation of urokinase from other sources, as from kidney tissue culture medium, or isolation of other plasminogen activators, such as streptokinase, likewise involves many steps, which are either costly, or may be associated with adverse immunological reactions. Moreover, the commercially available activators for clinical use (Abbokinase and Streptokinase) are known to have a low affinity for fibrin clots and therefore may not be optimally effective or may be associated with adverse side effects due to generalized proteolysis.

References regarding prior isolation of urokinase are the following:

(a) White, W. F.; Barlow, G. H.; Mozen, M.M.; The Isolation and Characterization of Plasminogen Activators [Urokinase] from Human Urine. Biochemistry, Vol. 5, pp. 2,160–2,169, 1966;

(b) Pye, E. K.; Maciag, T.; Kelly, P.; Iyzinger, M. R.; Purification of Urokinase by Affinity Chromotography In: Thrombosis and Urokinase, Eds. R. Paoletti and S. Sherry. Academic Press, London, New York, San Francisco 1977.

SUMMARY OF THE INVENTION

The present invention overcomes the above problems and makes it possible to isolate relatively large quantities of plasminogen activator from comparatively small quantities of starting material. Also the invention provides a new class of therapeutic and diagnostic agents in the form of a plasminogen activator characterized by strong affinity for fibrin.

According to the present invention plasminogen activator is isolated from urine or tissue culture medium by providing a solid, adsorptive matrix, (preferably diatomaceous earth), having fibrin on its surface, exposing a mother liquid based on urine or culture to the fibrin-containing matrix, whereby plasminogen activator molecules in the mother liquid which have affinity for fibrin are bound to molecules of fibrin, removing the remaining mother liquid, and separating the plasminogen activator from the fibrin-containing matrix.

The invention is based on the discovery that fibrin precipitated on a solid adsorptive matrix retains considerable affinity for certain plasminogen activators especially for a species of urokinase here designated as, having "high affinity". In contrast, if fibrin is covalently attached to activated agarose (i.e. agarose activated by cyanogen bromide) such affinity for the plasminogen activator does not then occur. While the cause for this difference is not experimentally proven, we now believe that fibrin precipitated on an adsorptive matrix without covalent bonding leaves free certain ϵ-amino groups of lysine residues of the fibrin. These ϵ-amino groups of lysine residues are believed to contribute to the newly-discovered affinity. In contrast, if the fibrin is covalently attached to activated agarose, the ϵ-amino groups of the lysine residues may be covalently linked to the agarose in such a manner as to substantially block the affinity. It is apparently for such reasons that the existence of a high affinity urokinase has been overlooked.

In preferred embodiments of the method of isolation of the invention a number of further conditions are preferred. The plasminogen activator is exposed to the fibrin-containing matrix by stirring fibrin-solid particles into a batch of liquid in which the plasminogen activator is present. The activator bound to the fibrin that is precipitated on the solid matrix is eluted from the fibrin surface. The eluate containing plasminogen activator eluted from the fibrin surface is passed through a gel filtration column to separate the high affinity plasminogen activator from the eluting agents and fibrin contaminants.

Preferably, for providing the solid matrix with fibrin on its surface, fibrinogen is treated with thrombin in the presence of the matrix in a manner to precipitate fibrin upon the matrix. Preferably this is done by exposing the adsorptive matrix surface to excess fibrinogen in a buffer, in quantity sufficient to effectively cover all adsorptive surface, and thereafter introducing thrombin in a buffer to convert fibrinogen to fibrin, whereby the adsorptive surface can be effectively fully occupied by fibrin.

Furthermore, according to a specific aspect of the invention, for isolating high affinity urokinase, the invention comprises providing an adsorptive solid matrix, preferably diatomaceous earth particles, precipitating fibrin on its surface by treating fibrinogen with thrombin in the presence of the matrix, exposing urine or tissue culture medium to the fibrin-containing matrix whereby urokinase of the species which has the discovered high affinity towards fibrin is bound to it, removing the unbound material with a buffer solution, separating the high affinity urokinase from the fibrin first by eluting the urokinase from the fibrin surface by an eluant agent containing a member from the group consisting of arginine, lysine and ϵ-amino-caproic acid in an aqueous solution and thereafter separating the urokinase from the agent.

In this method preferably the urine or tissue culture medium is exposed to the fibrin-carrying matrix by mixing particles with the urine or tissue culture medium and the liquid is removed by decantation and filtration followed by repeated washing of the fibrin matrix and bound activator with a buffer.

A new product according to the invention is high affinity plasminogen activator from urine and culture produced by the above method.

An improved thrombolytic agent according to the invention consists essentially of urokinase that has high affinity for fibrin, and made available to the physician in lyophilized form.

Specifically a new product is provided comprising a plasminogen activator isolated from a biological source such as urine or culture. The particular characteristics of this new product include a molecular weight of about 56,000 Daltons, a specific activity of 40,000–50,000 CTA units/mg when assayed on a fibrin plate, and the appearance of a single chain structure corresponding to a molecular weight of 56,000 Daltons as evidenced by a single protein band on 7.5 percent polyacrylamide gel when sodium dodecyl sulfate-gel electrophoresis is performed on the new product in the unreduced state. The product retains the appearance of a single chain structure as evidenced by a single band on 7.5 percent polyacrylamide gel when sodium dodecyl sulfate-gel electrophoresis is performed on the product which has been reduced by 0.1M dithiothreitol. Most importantly, the new product displays a substantial binding affinity for fibrin as evidenced by its high affinity for fibrin celite (fibrin precipitated on diatomaceous earth).

A plasminogen activator tracer for detecting blood clots according to the invention consists essentially of a high affinity plasminogen activator to which is attached a radioactive label, such as Iodine or Technitium. The characteristics of the high affinity plasminogen activator include a molecular weight of about 56,000 Daltons, a specific activity of 40,000–50,000 CTA units/mg when assayed on a fibrin plate, and the appearance of a single chain structure corresponding to a molecular weight of 56,000 Daltons as evidenced by a single protein band on 7.5 percent polyacrylamide gel when sodium dodicyl sulfate-gel electrophoresis is performed on the new product in the unreduced state. The plasminogen activator retains the appearance of a single chain structure as evidenced by a single band on 7.5 percent polyacrylamide gel when sodium dodecyl sulfate-gel electrophoresis is performed on the plasminogen activator which has been reduced by 0.1M dithiothreitol. Most importantly, the plasminogen activator displays a substantial binding affinity for fibrin as evidenced by its high affinity for fibrin celite. The high affinity that the plasminogen activator has for fibrin is the property that makes it, when radiolabelled, a new diagnostic agent for specific detection of fibrin thrombi through nuclear scanning.

GENERAL PRINCIPLES

The procedure utilizes properties of certain plasminogen activators to bind to fibrin. This principle is applied, in the example below, to the isolation of a plasminogen activator from urine which has a high affinity towards fibrin (High Affinity Urokinase, HAUK), but is also applicable to the extraction of high affinity plasminogen activators from other sources such as kidney tissue culture medium extracts.

The procedure utilizes a matrix consisting of material with the property to absorb fibrinogen. In the preferred example below, diatomaceous earth. Celite, was shown to be suitable for this purpose. A powdered form of this material is used in order to provide a large surface area. After this matrix is mixed with fibrinogen, the latter is converted to fibrin by exposure to thrombin, resulting in the precipitation of fibrin on the matrix. This particular matrix circumvents the formation of a gel which normally forms when fibrinogen is exposed to thrombin. When fibrin-Celite is stirred in urine, the HAUK is bound to the affinity matrix. Subsequently, the bound activator is removed from fibrin-Celite by washing with an eluant. The eluted HAUK is contaminated only by a small amount of fibrin, washed off from the column by the eluant, which along with the eluant material is easily separated by gel filtration. The final solution containing the activator is then lyophilized.

METHOD 10 g powdered diatomaceous earth (Celite Analytical filter aid, Fisher Scientific Co.), the matrix, is washed with distilled water and mixed with 2 percent human fibrinogen (Kabi, Stockholm, Sweden) in 25 ml buffer (0.05M sodium phosphate, pH 7.4 containing 0.1M NaCl and 1 m M EDTA). Thrombin (Parke Davis, Bovine topical) 100$\mu$ in 1 ml of buffer is added with constant stirring at room temperature to ensure good mixing to prevent agglutination of the fibrin-matrix. After 30 minutes, the fibrin-matrix is filtered through a sintered glass funnel and washed thoroughly with the same buffer (1 liter) followed by a buffer containing 0.2M arginine. A final washing is performed with 0.05M sodium phosphate buffer pH 7.4 containing 1 m M EDTA and 0.3M NaCl. The washed fibrin-matrix (15 ml of the settled volume) is added to 1 liter of fresh human urine and the mixture stirred for one hour in cold (4° C.). After filtration, the fibrin-matrix is packed in a column, washed with the equilibration buffer (8–10 column volumes). The activator is then eluted from the fibrin with arginine (0.2M in the above buffer) in a single sharp peak. Alternatively, elution may be accomplished with lysine or $\epsilon$-amino-caproic acid. The arginine and any fibrin derivatives contaminating the activator are then removed by gel filtration on Sephadex G-100 (Pharmacia Chemicals, Upsala, Sweden) and then the solution containing the activator is lyophilized.

RESULTS

Approximately 12.00–30.00 CTA units of HAUK are obtained from 1 liter of fresh human urine. The molecular weight of HAUK was determined to be approximately 56,000 Daltons by gel-filtration on Sephadex G-200 superfine [For technique, see P. Andrews, Methods Biochem. Anal. 8, 1–53 (1970)]. The HAUK material converted plasminogen to plasmin as demonstrated by a chromogenic synthetic substrate. On a plasminogen-rich fibrin plate, it induced rapid lysis of fibrin. It displays a specific activity of 40,000–50,000 CTA units/mg when assayed on the fibrin plate. [For technique, see P. Brakman, "Fibrinolysis: A Standardized Fibrin Plate Method and a Fibrinolytic Assay of Plasminogen" published by Scheltima and Holkema, Amsterdam, pp. 1–124 (1967)].

COMPARISON OF HAUK WITH COMMERCIAL UROKINASE (ABBOTT)

Two principle differences and one common property were found which are summarized in the table below.

TABLE

| | Urokinase (Abbott) | High Affinity Urokinase HAUK (Present Invention) |
|---|---|---|
| MOLECULAR WEIGHT (Daltons) | 36,000 | 56,000 |
| FIBRIN BINDING (Fibrin-Celite Column) | <5% | 100% |

TABLE-continued

| | Urokinase (Abbott) | High Affinity Urokinase HAUK (Present Invention) |
|---|---|---|
| BINDING TO SEPHAROSE-FIBRIN | <1% | <1% |

In addition, more effective lysis of fibrin under physiological conditions was found for HAUK compared to the commercial urokinase.

The commercial urokinase (Abbott) contains, predominantly of the low molecular weight form. The fraction of high molecular weight urokinase found in the commercial urokinase (Abbott) appears to be a two chain structure as evidenced by two protein bands after reduction and sodium dodecyl sulfate-gel electrophoresis [For technique see K. Weber and M. Osborn, The Proteins, eds. Neurath, H. and Hill, L. L. (Academic Press, New York) Vol. 1. pp. 179-223 (1975)]. This high molecular weight form of urokinase has low affinity for fibrin whereas the low molecular weight urokinase has none. Cumulatively, the commercial urokinase mixture of high and low molecular weight urokinases are known to have a very low affinity for fibrin, as noted above.

HAUK has a molecular weight of about 56,000 Daltons, as comparable to that of the high molecular weight form in commercial urokinase. However, HAUK appears as a one chain structure as evidenced by one protein band after reduction with 0.1M dithiothreitol and sodium dodecyl sulfate-gel electrophoresis on 7.5 percent polyacrylamide gel. [Ibid., Weber et al.]

Binding of HAUK, the high molecular weight single chain species of urokinase of the invention, to fibrin celite under conditions used for its adsorption indicates its high binding affinity for fibrin.

It is believed that HAUK, which we for the first time have isolated, retains the native molecular form. The few step, fast method of isolation enables the single chain molecular structure to be retained.

On the other hand, the relatively slow, many step procedures of the prior art, we believe, have resulted in degradation of the molecule, and have resulted in the two chain structure and low affinity for fibrin.

FEATURES OF THE METHOD

The present method has a number of advantages over existing procedures:

1. It is a rapid, single-step, instead of a lengthy, multistep isolation procedure. The lengthy procedure currently in use allows undesirable denaturation, autodegradation, or degradation of urokinase by other proteolytic enzymes.

2. The method separates the high affinity from low affinity plasminogen activator, and establishes for the first time that fresh urine contains a high affinity urokinase (40 to 80 percent of the total urokinase, depending on the subject).

3. The method provides a high yield (about 60 percent) of the total HAUK in urine and with no low-affinity urokinase present. In contrast urokinase that is presently commercially available for clinical use (Abokinase, Abbott) has essentially no HAUK and is a low-affinity plasminogen activator.

APPLICATIONS

I. General

Because the described extraction method is economical and rapid, it should provide a relatively cheap and abundant supply of human plasminogen activator characterized by a high affinity for fibrin for both scientific research and clinical purposes.

II. Therapy

The two commercially available plasminogen activators Streptokinase (Hoechst and Kabi) and Urokinase (Abbott) which have received FDA approval for the thrombolytic therapy of pulmonary embolism are low affinity activators. As a result, a large amount of activator (100,000-200,000 CTA $\mu$/hour) must be infused to achieve clot lysis. Since plasmin is an enzyme with broad specificity, the effect of infusing these activators is an undesired state of generalized proteolysis which degrades several plasma proteins (fibrinogen, factors V and VIII).

By contrast, the HAUK discovered and efficiently isolated according to the present invention, because of its affinity for fibrin, will provide a much more specific fibrinolysis at lower concentrations of the activator.

III. Diagnosis

The fibrin binding properties of HAUK can also be utilized for the detection of intravascular clots or thrombi. By attaching an appropriate radioactive isotope (e.g. $^{125}$Iodine or Technitium) to the molecule and then by intravenous injection of the labelled HAUK, it is possible to identify intravascular fibrin by radionuclear scanning. For example, the labelled HAUK can be used for the specific detection of pulmonary emboli (lung clots) by lung scanning. This diagnosis is notoriously difficult to make by current methods because they are too non-specific.

Prior efforts to employ radioactively-labelled plasminogen activators for radionuclear scanning are believed to have been relatively unsuccessful because the plasminogen activators used lacked the essential property of having high affinity for fibrin. References regarding such prior efforts are (a) Millar, W. T. and Smith, J. F. B., Localization of Deepvenous Thrombosis Using Technitium 99 m—labelled Urokinase (preliminary communication), Lancet Vol. 2, p. 695-696, 1974; (b) Kempi, V.; Van DerLinden, W.; and van Scheele, C.; Diagnosis of Deep Vein Thrombosis with 99 mTc—streptokinase; A Clinical Comparison with Phlebography, British Medical Journal, Vol. 2, p. 748-749, 1974.

What is claimed is:

1. The method of isolating a plasminogen activator from urine or culture medium, comprising providing an adsorptive matrix having fibrin precipitated on its surface, exposing a mother liquid based upon urine or culture medium and containing high fibrin-affinity plasminogen activator to the fibrin-containing matrix, whereby those plasminogen activator molecules which have high affinity therefor are bound to molecules of fibrin, removing the remaining mother liquid, and separating the plasminogen activator from the fibrin.

2. The method of claim 1 wherein the plasminogen activator is eluted from the fibrin surface by an eluant agent solution containing a member of the group consisting of arginine, lysine, and ϵ-amino-caproic acid.

3. The method of claim 1 wherein said matrix comprises diatomaceous earth.

4. The method of claim 1 wherein, for providing said matrix with fibrin on its surface, fibrinogen is treated with thrombin in the presence of the said matrix in a manner to cause fibrin to be precipitated upon said matrix without gel formation.

5. The method of claim 4 comprising exposing the adsorptive surface of said matrix to fibrinogen in quantity sufficient of effectively cover said adsorptive surface, thereafter introducing thrombin to convert said adsorbed fibrinogen to fibrin, whereby said adsorptive surface is effectively fully occupied by adsorbed fibrin.

6. The method of isolating urokinase comprising providing a solid matrix with fibrin by treating fibrinogen with thrombin in the presence of said matrix to cause fibrin to be in an absorbed state upon said substrate, exposing urine or culture medium to the substrate whereby a species of urokinase which has affinity towards fibrin is bound to the fibrin, removing the unbound material by washing with a buffer solution, separating the urokinase from the fibrin first by eluting the urokinase from the fibrin surface by an eluant agent comprising a member of the group consisting of arginine, lysine, ϵ-amino-caproic acid, and thereafter separating said urokinase from said agent.

7. The method of claim 1 or 6 wherein said matrix comprises particles wherein the liquid is exposed to said fibrin-carrying matrix by mixing said particles with said liquid.

8. The method of claim 1 or 6 wherein said liquid is removed by decanting and filtering followed by repeated washing with a buffer.

9. A plasminogen activator enzyme concentrate isolated from a biological source by the methods of any of the claims 1–6 and comprising urokinase (human) of molecular weight of about 56,000 Daltons, having high affinity for binding to fibrin on an adsorptive matrix and having the appearance of a single chain molecular structure.

10. [A] *Urokinase* plasminogen activator isolated from [a biological source such as] urine or culture consisting essentially of urokinase (human) characterized as (a) having a molecular weight of about 56,000 Daltons *as determined by gel-filtration*, (b) [having a specific activity of less than 50,000 CTA units/mg when assayed on a fibrin plate, (c) having the appearance of a single chain structure corresponding to a molecular weight of 56,000 Daltons as evidenced by] *appearing as* a single protein band *corresponding to a molecular weight of about* 56,000 Daltons on 7.5 percent polyacrylamide gel when sodium dodecyl sulfate-gel electrophoresis is performed on unreduced urokinase, [d] (*c*) retaining [the] said appearance [of a single chain structure as evidenced by a single protein band on 7.5 percent polyacrylamide gel when sodium dodecyl sulfate-gel] *when said* electrophoresis is performed on urokinase which has been reduced by 0.1M dithiothreitol *thereby indicating its single chain structure* and [(e)] (*d*) displaying a high binding affinity for fibrin precipitated on diatomaceous earth.

*11. The urokinase of claim 10 in lyophilized form.*

* * * * *